United States Patent [19]
Fischer et al.

[11] Patent Number: 5,543,572
[45] Date of Patent: Aug. 6, 1996

[54] MONOCARBOXAMIDES OF POLYAMINES

[75] Inventors: Walter Fischer, Reinach; Christine Helbling, Birsfelden, both of Switzerland

[73] Assignee: Ciba-Geigy Corporation, Tarrytown, N.Y.

[21] Appl. No.: 377,719

[22] Filed: Jan. 24, 1995

[30] Foreign Application Priority Data

Jan. 28, 1994 [CH] Switzerland ................. 268/94

[51] Int. Cl.$^6$ .................................. C07C 233/65
[52] U.S. Cl. ..................... 564/179; 554/35; 554/51; 564/170; 564/176; 564/177; 564/204; 564/207; 564/192
[58] Field of Search ................... 564/179, 177, 564/204, 215, 170, 176, 207, 192; 554/35, 51

[56] References Cited

U.S. PATENT DOCUMENTS 4,562,201  12/1985  Stout et al. ................. 514/422

FOREIGN PATENT DOCUMENTS 0554823  8/1993  European Pat. Off. .
57-91963  6/1982  Japan .

OTHER PUBLICATIONS

Chemical Abstract vol. 97, No. 25, 1982 215723b.
Technical Information Sheet Ancamine X2280, Mar. 11, 1992.

*Primary Examiner*—Shailendra Kumar
*Attorney, Agent, or Firm*—William A. Teoli, Jr.; Kevin T. Mansfield

[57] ABSTRACT

Monocarboxamides of formula I

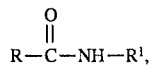

wherein R is a radical of formula

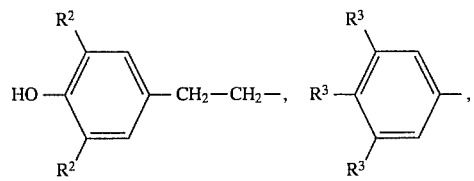

$C_9$–$C_{19}$alkyl, $C_9$–$C_{19}$alkenyl or $C_9$–$C_{19}$alkdienyl, wherein each $R^2$ independently of the other is a hydrogen atom or $C_1$–$C_4$alkyl, each $R^3$ independently of one another is a hydrogen atom or a hydroxyl group and at least one $R^3$ is a hydroxyl group, and $R^1$ is a radical of formula

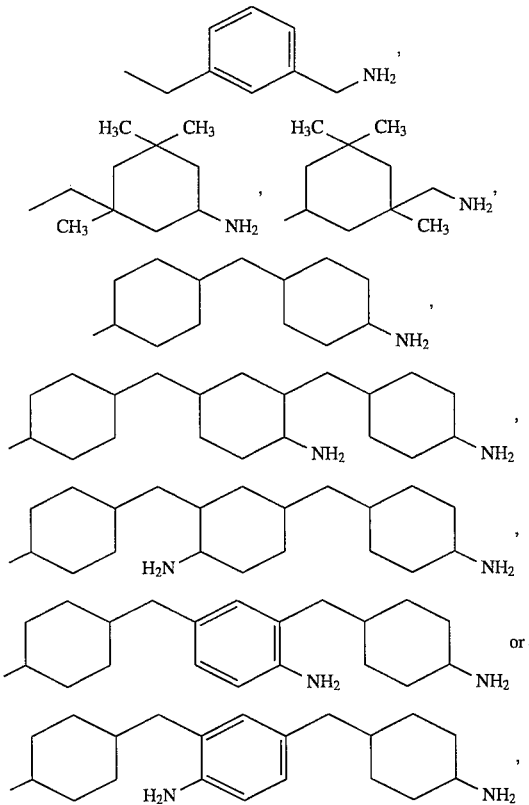

are suitable for curing epoxy resins, in

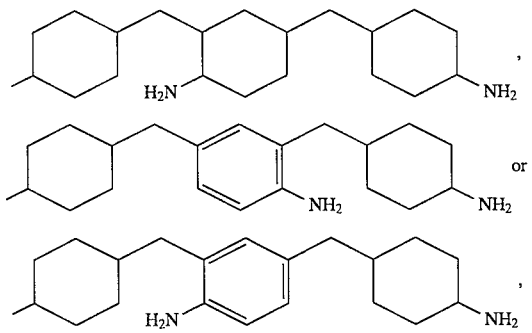

are suitable for curing epoxy resins, in particular for cold curing.

5 Claims, No Drawings

MONOCARBOXAMIDES OF POLYAMINES

The present invention relates to novel monocarboxamides of specific diamines and triamines, to curable epoxy resin compositions comprising said novel monocarboxamides and to the moulded objects, in particular coatings, obtained from said curable epoxy resin compositions by curing.

To prepare chemical-resistant coatings based on epoxy resins it is preferred to use liquid polyamine hardeners such as formulated mixtures derived from 4,4'-diaminodiphenylmethane. This hardener, however, is held to be mutagenic and carcinogenic and in the USA, for example, the OSHA (Occupational Safety and Health Administration), Final Rule in the Federal Register on the Use of Methylene Dianiline, has imposed stringent restrictions on its use. Likewise, the Swiss Federal Office of Health has classified this hardener as a class 1* poison (carcinogen) in the Poisons List 1 (1991 issue). Hence there is a need to provide other aminic hardeners for epoxy resin coatings.

A liquid polyamine derived from polycyclic polyamines and available from Anchor Chemical under the trade name Ancamine X2280 is suitable for the production of epoxy resin coatings having good resistance to chemicals except for carboxylic acids, for example acetic acid.

It has now been found that specific novel monocarboxamides obtained by reacting specific hydroxymonocarboxamides or esters thereof with specific di- or triamines impart to epoxy resin coatings an enhanced resistance to chemicals, especially to carboxylic acids.

Accordingly, the present invention relates to hydroxy group-containing monocarboxamides of formula I

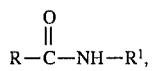

wherein R is a radical of formula

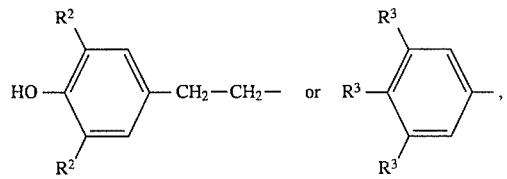

a $C_9$–$C_{19}$alkyl, $C_9$–$C_{19}$alkenyl or a $C_9$–$C_{19}$alkdienyl, wherein each $R^2$ independently of the other is a hydrogen atom or $C_1$–$C_4$alkyl, each $R^3$ independently of one another is a hydrogen atom or a hydroxyl group, and at least one $R^3$ is a hydroxyl group, and $R^1$ is a radical of formula

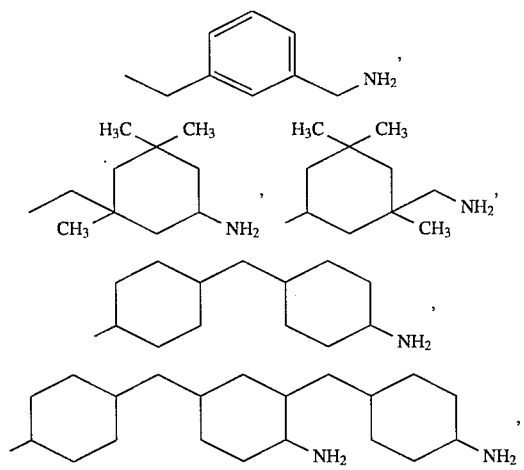

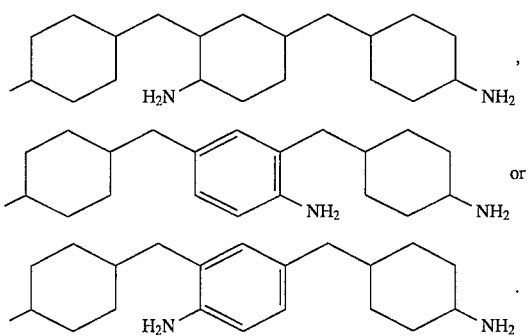

Those novel hydroxyl group-containing monocarboxamides of formula I are preferred, wherein R is a radical of formula

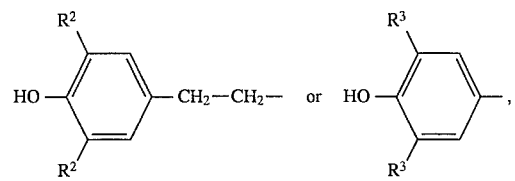

a $C_{15}$–$C_{17}$alkyl or $C_{15}$–$C_{17}$alkenyl, wherein each $R^2$ is tert-butyl and each $R^3$ is a hydrogen atom or a hydroxyl group.

In particular, R in formula I is a radical of formula

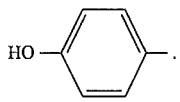

In the novel monocarboxamides, $R^1$ is preferably a radical of formula

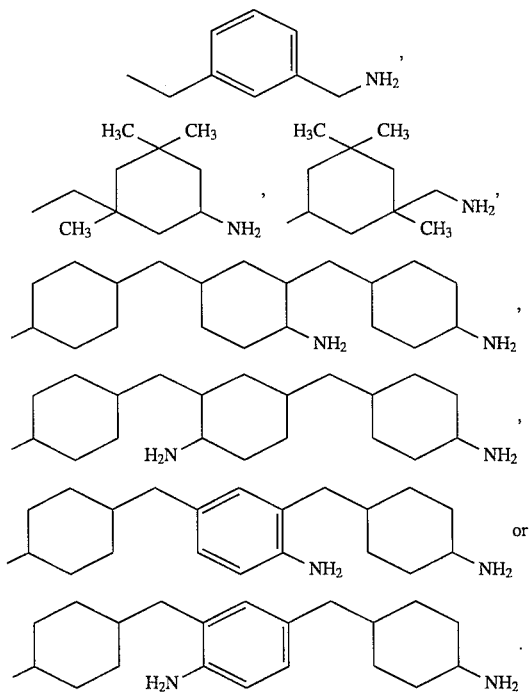

As mentioned at the outset, the novel compounds are useful aminic hardeners for epoxy resins.

The invention therefore also relates to a hardener for epoxy resins that comprises at least one compound of formula I.

The novel hardener may typically be prepared by reacting a monocarboxylic acid or an ester thereof of formula II

R—COOR⁴                    (II), wherein R has the same meaning as in formula I and $R^4$ is a hydrogen atom, $C_1$–$C_6$alkyl or phenyl, with a di- or triamine of formula III

$H_2N$—$R^1$                  (III), wherein $R^1$ has the same meaning as in formula I, at elevated temperature, using 2 to 10 mol of a compound of formula III per 1 mol of a compound of formula II.

This reaction is usually carried out in the temperature range from 80° to 200° C. The preferred temperature range for the reaction of the monocarboxylic acid with the di- or triamine is from 160° to 200° C., and for the reaction of the monocarboxylate with the di- or triamine from 100° to 180° C.

An equivalent excess of the di- or triamine of formula III is preferably used in this reaction, so that essentially the corresponding diaminomonocarboxamides and triaminomonocarboxamides result in addition to excess di- and triamine. To use these reaction products as hardeners it is possible, but not necessary, to free said products from excess di- or triamine.

The reaction of the monocarboxylic acids or the esters thereof with the di- or triamines can also be carried out in the presence of additives such as solvents, e.g. butanol or xylene, accelerators such as salicylic acid, nonyl phenol, perchlorates or nitrates of alkali metals or alkaline earth metals, flexibilisers such as polyethylene glycols, flow control agents such as benzyl alcohol, pigments, fillers or antioxidants.

The reaction can also be carried out simultaneously or in succession with different di- and/or triamines and different monocarboxylic acids or esters thereof to give the corresponding product mixtures.

The monocarboxylic acids of formula II and the di- and triamines of formula III are known compounds, and some are commercially available.

As mentioned at the outset, the novel monocarboxamides may be used for hardening customary epoxy resins.

The invention accordingly also relates to curable compositions comprising (a) an epoxy resin containing more than one 1,2-epoxy group in the molecule, and (b) at least one novel compound of formula I.

Epoxy resins (a) which may suitably be used in the novel curable compositions are the standard epoxy resins of epoxy resin technology. Typical examples of epoxy resins are:

I) Polyglycidyl and poly(β-methylglycidyl) esters which are obtainable by reacting a compound containing at least two carboxyl groups in the molecule and epichlorohydrin or β-methylepichlorohydrin. The reaction is conveniently carried out in the presence of a base.

Compounds containing at least two carboxyl groups in the molecule may suitably be aliphatic polycarboxylic acids. Examples of such polycarboxylic acids are oxalic acid, succinic acid, glutaric acid, adipic acid, pimelic acid, sebacic acid, suberic acid, azelaic acid or dimerised or trimerised linoleic acid. It is, however, also possible to use cycloaliphatic polycarboxylic acids such as tetrahydrophthalic acid, 4-methyltetrahydrophthalic acid, hexahydrophthalic acid or 4-methylhexahydrophthalic acid. Aromatic polycarboxylic acids can also be used, typically phthalic acid, isophthalic acid and terephthalic acid.

II) Polyglycidyl or poly(β-methylglycidyl) ethers which are obtainable by reacting a compound containing at least two free alcoholic hydroxyl groups and/or phenolic hydroxyl groups and epichlorohydrin or β-methylepichlorohydrin, under alkaline conditions or in the presence of an acid catalyst and subsequent treatment with an alkali.

The glycidyl ethers of this type are typically derived from acyclic alcohols, typically from ethylene glycol, diethylene glycol and higher poly(oxyethylene) glycols, 1,2-propanediol or poly(oxypropylene)glycols, 1,3-propanediol, 1,4-butanediol, poly(oxytetramethylene) glycols, 1,5-pentanediol, 1,6-hexanediol, 2,4,6-hexanetriol, glycerol, 1,1,1-trimethylolpropane, pentaerythritol, sorbitol, as well as from polyepichlorohydrins. They may also be derived from cycloaliphatic alcohols such as 1,4-cyclohexanedimethanol, bis(4-hydroxycyclohexyl)methane or 2,2-bis(4-hydroxycyclohexyl)propane, or they contain aromatic nuclei such as N,N-bis(2-hydroxyethyl)aniline or p,p'-bis(2-hydroxyethylamino)diphenylmethane.

The glycidyl ethers may also be derived from mononuclear phenols, typically from resorcinol or hydroquinone, or they are derived from polynuclear phenols such as bis(4-hydroxyphenyl)methane, 4,4'-dihydroxybiphenyl, bis(4-hydroxyphenyl)sulfone, 1,1,2,2-tetrakis(4-hydroxyphenyl)ethane, 2,2-bis(4-hydroxyphenyl)propane, 2,2-bis(3,5-dibromo-4-hydroxyphenyl)propane, as well as from novolaks obtainable by condensation of aldehydes such as formaldehyde, acetaldehyde, chloral or furfuraldehyde, with phenols such as phenol, or with phenols which are substituted in the nucleus by chlorine atoms or $C_1$–$C_9$alkyl groups, for example 4-chlorophenol, 2-methylphenol or 4-tert-butylphenol, or by condensation with bisphenols of the type cited above.

III) Poly-(N-glycidyl) compounds obtainable by dehydrochlorination of the reaction products of epichlorohydrin with amines which contain at least two amino hydrogen atoms. These amines are typically aniline, n-butylamine, bis(4-aminophenyl)methane, m-xylylenediamine or bis(4-methylaminophenyl)methane. The poly(N-glycidyl) compounds also include triglycidyl isocyanurate, N,N'-diglycidyl derivatives of cycloalkylene ureas such as ethylene urea or 1,3-propyleneurea, and diglycidyl derivatives of hydantoins, typically of 5,5-dimethylhydantoin.

IV) Poly(S-glycidyl) compounds, preferably bis(S-glycidyl) derivatives which are derived from dithiols such as 1,2-ethanediol or bis(4-mercaptomethylphenyl)ether.

V) Cycloaliphatic epoxy resins, including bis(2,3-epoxycyclopentyl) ether, 2,3-epoxycyclopentyl glycidyl ether, 1,2-bis(2,3-epoxycyclopentyloxy)ethane or 3,4-epoxycyclohexylmethyl-3',4'-epoxycyclohexanecarboxylate.

It is also possible to use epoxy resins in which the 1,2-epoxy groups are attached to different hetero atoms or functional groups. These compounds typically comprise the N,N,O-triglycidyl derivative of 4-aminophenol, the glycidyl ether-glycidyl ester of salicylic acid, N-glycidyl-N'-(2-glycidyloxypropyl)-5,5-dimethylhydantoin or 2-glycidyloxy-1,3-bis(5,5-dimethyl-1-glycidylhydantoin-3-yl)propane.

It is preferred to use as epoxy resin (a) in the novel curable compositions a liquid or viscous polyglycidyl ether or ester, preferably a liquid or viscous diglycidyl ether of a bisphenol.

The aforementioned epoxy compounds are known and some are commercially available. Mixtures of epoxy resins can also be used.

The amount of hardener will depend on the chemical nature of the hardener and on the desired properties of the curable mixture and the hardened product. The maximum amount can be readily determined. The amount used is normally 0.75 to 1.25 equivalents of active hydrogen bound to amino nitrogen atoms per 1 epoxide equivalent.

The novel compositions can be prepared in conventional manner by mixing the components by hand stirring or using known mixing aggregates, typically stirrers, kneaders or roll mills.

Depending on the utility, the customary modifiers can be added to the compositions of this invention, including typically fillers, pigments, dyes, flow control agents or plasticisers.

The novel compositions advantageously have a comparatively low carbonising tendency, i.e. at low temperature and at high humidity the compositions do not become turbid through the uptake of $CO_2$ from the atmosphere and no crystallinity occurs after reaction of the $CO_2$ with the polyamines.

The novel compositions can be cured in per se known manner in one or more steps. The cure is usually effected at room temperature or below room temperature or by heating the compositions to temperatures up to 120° C., preferably in the temperature range from 5° to 50° C. To obtain a good cure of the novel compositions at low temperature, for example in the range from 5° to 50° C., it is possible to use the compositions with curing accelerators based on tertiary amines and/or phenols and/or alkali metal or alkaline earth metal salts, typically 2,4,6-tris(dimethylaminomethyl)phenol, nonyl phenol, calcium or magnesium nitrate.

The invention further relates to the moulded objects or coatings obtained by curing the novel compositions.

As mentioned at the outset, the moulded objects or coatings obtained from the compositions of this invention have superior resistance to chemicals, especially to carboxylic acids, for example aqueous acetic acid having a concentration of up to 30% by weight.

Preparation of the polyaminoamides:

EXAMPLE 1

97.8 g (304.1 mmol) of Ancamine® X2168 (MPCA) and 47.9 g of benzyl alcohol are heated to 120° C., and to this mixture are added 14.0 g (76 mmol) of methyl gallate. This mixture is stirred for 2.5 hours (h) at 160° C., during which time methanol is distilled from the mixture. The mixture is cooled, affording 155.0 g (99% of theory) of a product mixture consisting of 30% by weight of benzyl alcohol and 70% by weight of a polyamine mixture which, in addition to excess MPCA, mainly comprises the monoamides of formulae

EXAMPLE 2

34.9 g (108,6 mmol) of Ancamine® X2168 (MPCA) and 20.6 g of benzyl alcohol are heated to 160° C. To this mixture are added 5.0 g (27.2 mmol) of methyl gallate and 8.05 g (27.2 mmol) of methyl oleate and the mixture is stirred for 5 h at 180° C. The mixture is cooled, affording 62.1 g (93% of theory) of a product mixture consisting of 30% by weight of benzyl alcohol and 70% by weight of a polyamine mixture which, in addition to excess MPCA, maily comprises the monoamides of formulae

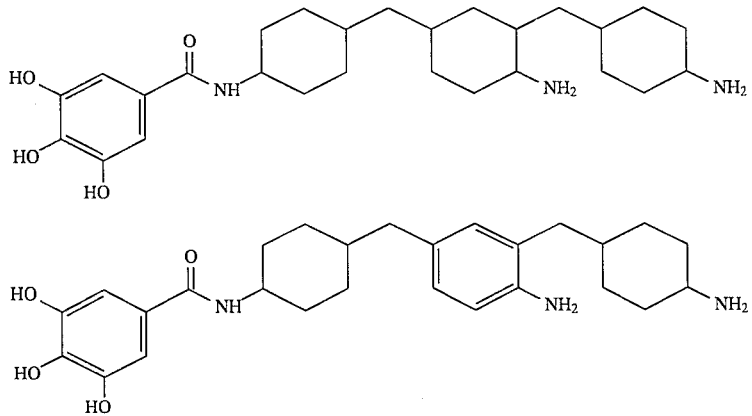

and their structural isomers and stereoisomers.

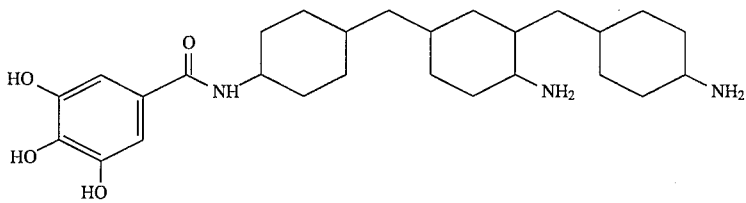

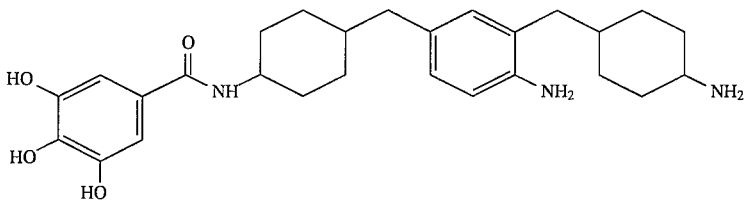

and

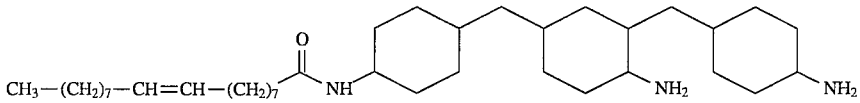

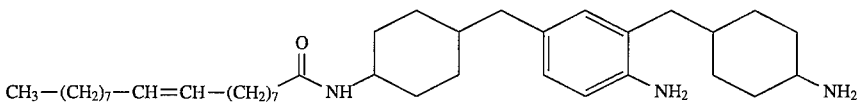

and their structural isomers and stereoisomers.

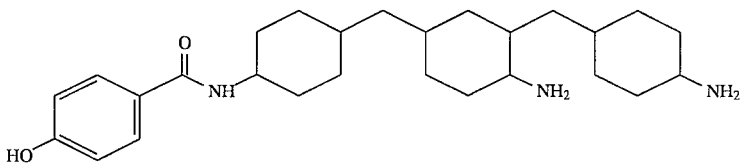

and

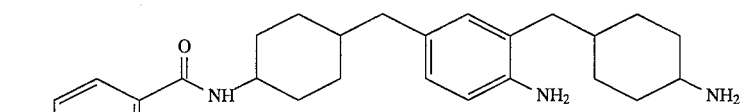

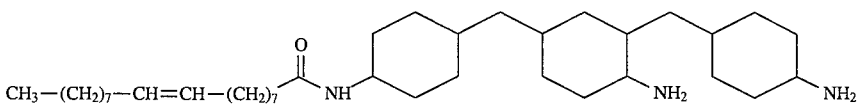

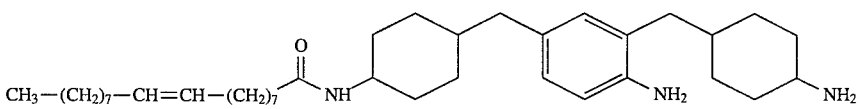

and their structural isomers and stereoisomers.

EXAMPLE 3

42.3 g (131.4 mmol) of Ancamine® X2168 (MPCA) and 24.5 g of benzyl alcohol are heated to 160° C. To this mixture are added 5.0 g (32.9 mmol) of methyl-4-hydroxybenzoate and 9.74 g (32.9 mmol) of methyl oleate and the mixture is then stirred for 7.5 h at 180° C. The mixture is cooled, affording 77.1 g (97% of theory) of a product mixture consisting of 30% by weight of benzyl alcohol and 70% by weight of a polyamine mixture which, in addition to excess MPCA, mainly comprises the monoamides of formulae

EXAMPLE 4

57.4 g (421.6 mmol) of m-xylylenediamine (MXDA) and 25 g (84.3 mmol) of methyl oleate are mixed and the mixture is stirred for 5 h at 170° C., during which time methanol is distilled from the mixture. The mixture is cooled, affording a polyamine mixture which, in addition to excess MXDA, mainly comprises the monoamide of formula

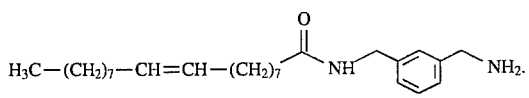

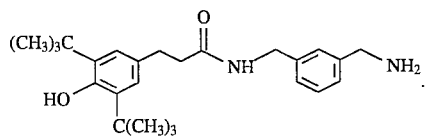

EXAMPLE 5

55.5 g (407.3 mmol) of MXDA and 15.0 g (81.5 mmol) of methyl gallate are mixed and the mixture is stirred for 3 h at 160° C., during which time methanol is distilled from the mixture. The mixture is cooled, affording 66.1 g (97% of theory) of a greenish-yellow oil which, in addition to excess MXDA, mainly comprises the monoamide of formula

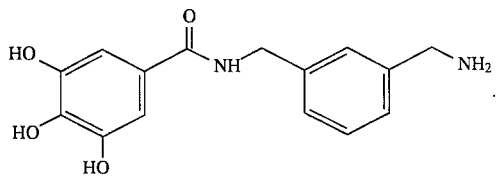

This product can be purified and isolated in the following manner: 2.2 g of the greenish-yellow oil obtained above are extracted with 2×40 ml of dioxane, during which time each of the dioxane phases is decanted off hot. The dioxane phases are cooled, decanted and dried under high vacuum, giving residues (total amount 840 mg) which, according to $^1$H-NMR- and mass spectra, consist of the compound of the formula cited above (in an amount of about 67 mol %) and MXDA (in an amount of about 33 mol %) (2:1 molecular complex).

EXAMPLE 6

A mixture of 20.0 g (58.7 mmol) of butyl stearate, 40.0 g (293.6 mmol) of MXDA and 25.7 g of benzyl alcohol is stirred for 15 h at 200° C., during which time some of the butanol that forms is distilled from the mixture. The mixture is cooled, affording 83.1 g (>100% of theory) of a semi-solid product mixture consisting of 30% by weight of benzyl alcohol and 70% by weight of a polyamine mixture which, in addition to excess MXDA, mainly comprises the monoamide of formula

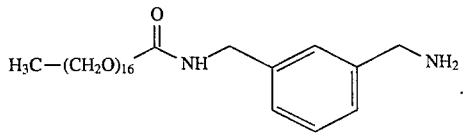

EXAMPLE 7

A mixture of 18.0 g (61.6 mmol) of methyl-3-[3,5-bis-(tert-butyl)-4-hydroxyphenyl]-propionate, 42.0 g (307.8 mmol) of MXDA and 25.7 g of benzyl alcohol is stirred for 8 h at 180° C., during which time methanol is distilled from the mixture. The mixture is cooled, affording 82.1 g (98% of theory) of a yellow oil consisting of 30% by weight of benzyl alcohol and 70% by weight of a polyamine mixture which, in addition to excess MXDA, mainly comprises the monoamide of formula

EXAMPLE 8

A mixture of 10.0 g (54.3 mmol) of methyl gallate, 37.0 g (217.2 mmol) of isophoronediamine (IPD) and 20.14 g of benzyl alcohol is stirred for 3 h at 160° C., during which time methanol is distilled from the mixture. The mixture is cooled, affording 63.6 g (97% of theory) of a dark oil consisting of 30% by weight of benzyl alcohol and 70% by weight of a polyamine mixture which, in addition to excess IPD, mainly comprises the monoamides of formulae

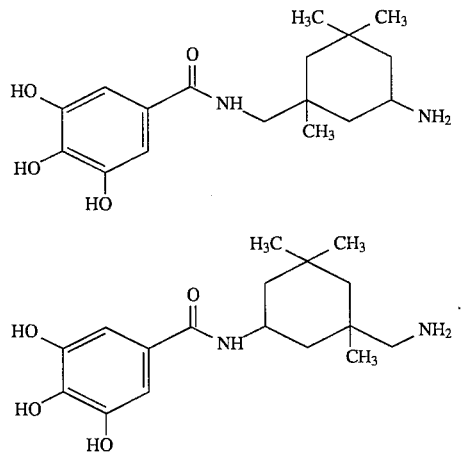

EXAMPLE 9

57.5 g (337.3 mmol) of IPD and 20.0 g (67.5 mmol) of methyl oleate are mixed and the mixture is stirred for 6 h at 170° C., during which time methanol is distilled from the mixture. The mixture is cooled, affording 76.3 g (>100%) of a product mixture which, in addition to excess IPD, mainly comprises the monoamides of formulae

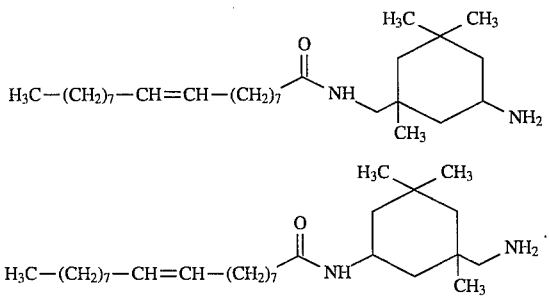

EXAMPLE 10

A mixture of 15.0 g (44.0 mmol) of butyl stearate, 37.5 g (220.2 mmol) of IPD and 22.5 g of benzyl alcohol is stirred for 20 h at 200° C., during which time some of the butanol that forms is distilled from the mixture. The mixture is cooled, affording 71.4 g (>100% of theory) of a product mixture consisting of 30% by weight of benzyl alcohol and 70% by weight of a polyamide mixture which, in addition to excess IPD, mainly comprises the products of formulae

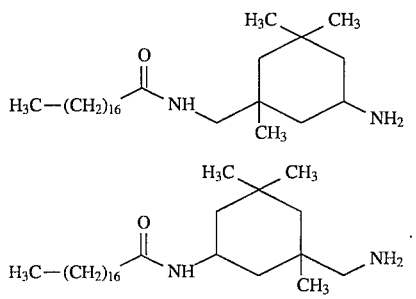

EXAMPLE 11

A mixture of 15.0 g (51.3 mmol) of methyl-3-[3,5-bis-(tert-butyl)-4-hydroxyphenyl-]-propionate, 43.7 g (2565 mmol) of IPD and 25.2 g of benzyl alcohol is stirred for 8.5 h at 180° C., during which time methanol is distilled from the mixture. The mixture is cooled, affording 79.3 g (96%) of a yellow oil consisting of 30% by weight of benzyl alcohol and 70% by weight of a polyamine mixture which, in addition to excess IPD, mainly comprises the products of formulae

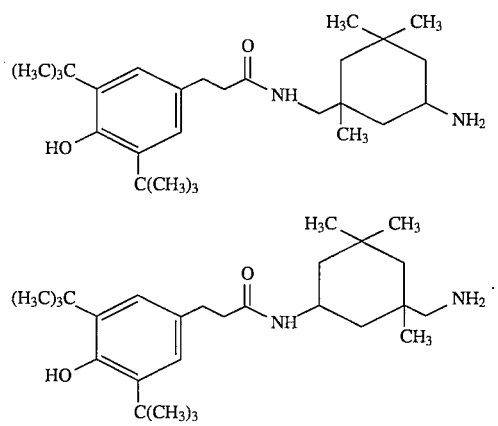

EXAMPLE 12

211.34 g (657.25 mmol) of Ancamine® X2168 (MPCA) and 10 1.5 g of benzyl alcohol are heated to 160° C. To this mixture are added 25 g (164.31 mmol) of methyl-4-hydroxybenzoate and the mixture is stirred for 8 h at 180° C., during which time methanol is distilled from the mixture. The mixture is cooled, affording 328.84 g (99%) of a product mixture consisting of 30% by weight of benzyl alcohol and 70% by weight of a polyamine mixture which, in addition to excess MPCA, mainly comprises the monoamides of formulae

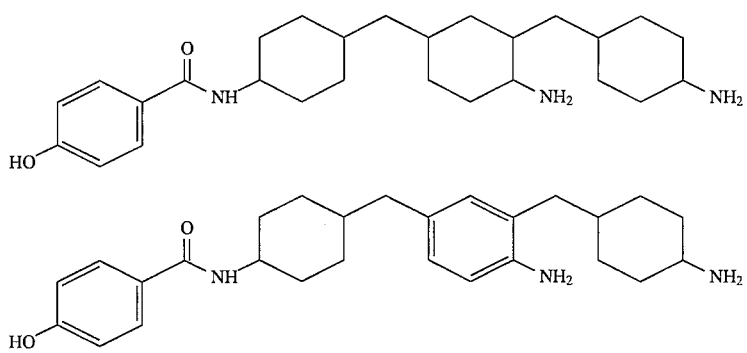

and their structural isomers and stereoisomers.

Use Examples

EXAMPLE I 2.5 g of the hardener obtained in Example 1 are thoroughly mixed with 5.0 g of a diglycidyl ether of bisphenol A (epoxy value=5.25–5.40 equivalents/kg; viscosity= 10000–12000 mPa.s). The clear mixture is applied with a brush to a sand-blasted, degreased steel plate or with a coating knife (0.20 mm) to a glass plate. The clear and hard layers that form after some hours at 20° C. have, after 1 day, a Persoz hardness of 266 s at 20° C. on the glass plate, measured with a TY 5853 pendulum damping tester (BYK-Chemie) according to Persoz. After a 7-day cure at 20° C. the Persoz hardness has increased to 326 s. The layer on the steel plate then resists contact with 10% aqueous acetic acid for at least 3 months without pitting or without peeling from the plate. The curable composition described above also cures satisfactorily at 20° C./100% relative humidity and at 5° C./45% relative humidity with no or only very minor surface haze.

EXAMPLE II 2.0 g of the hardener obtained in Example 1 and 0.5 g of the hardener obtained in Example 2 are thoroughly mixed with 5.0 g of a diglycidyl ether of bisphenol A (epoxy value=5.25–5.40 equivalents/kg; viscosity=10000–12000 mPa.s) and 0.5 g of 4-nonylphenol. The clear mixture is applied with a brush to a sand-blasted, degreased steel plate or with a coating knife (0.20 mm) to a glass plate. The clear and hard layers that form after some hours at 20° C. have, after 1 day, a Persoz hardness of 165 s at 20° C. on the glass plate, measured with a TY 5853 pendulum clamping tester (BYK-Chemie) according to Persoz. After a 7-day cure at 20° C. the Persoz hardness has increased to 268 s. The layer on the steel plate then resists contact with 10% aqueous acetic acid for at least 3 months without pitting or without peeling from the plate. The curable composition described above also cures satisfactorily at 20° C./100% relative humidity and at 5° C./45% relative humidity with no or only very minor surface haze.

If 4-nonylphenol is omitted from the above formulation, the Persoz hardness obtained after 1 day at 20° C. is 233 s, and after a 7-day cure at 20° C. the Persoz hardness is 297 s. The other properties mentioned, in particular the resistance to 10% acetic acid, are very similar.

EXAMPLE III 2.5 g of the hardener obtained in Example 3 are thoroughly mixed with 3.8 g of a diglycidyl ether of bisphenol A (epoxy value=5.25–5.40 equivalents/kg; viscosity= 10000–12000 mPa.s) and 1.0 g of 4-nonylphenol. The clear mixture is applied with a brush to a sand-blasted, degreased steel plate or with a coating knife (0.20 mm) to a glass plate. The clear and hard layers that form after some hours at 20° C. have, after 1 day, a Persoz hardness of 52 s at 20° C. on the glass plate, measured with a TY 5853 pendulum damping tester (BYK-Chemie) according to Persoz. After a 7-day cure at 20° C. the Persoz hardness has increased to 204 s. The layer on the steel plate then resists contact with 10% aqueous acetic acid for at least 3 months without pitting or without peeling from the plate. The curable composition described above also cures satisfactorily at 20° C./100% relative humidity and at 5° C./45% relative humidity with no or only very minor surface haze.

If 4-nonylphenol is replaced with 0.5 benzyl alcohol in the above formulation, the Persoz hardness obtained after 1 day at 20° C. is 32 s, and after a 7-day cure at 20° C. the Persoz hardness is 255 s. The other properties mentioned, in particular the resistance to 10% acetic acid, are very similar.

EXAMPLE IV 2.5 g of the hardener obtained in Example 12 are thoroughly mixed with 5.05 g of diglycidyl ether of bisphenol A (epoxy value=5.25–5.40 equivalents/kg; viscosity= 10000–12000 mPa.s) and 2.0 g of 4-nonylphenol. The clear mixture is applied with a brush to a sand-blasted, degreased steel plate or with a coating knife (0.20 mm) to a glass plate. The clear and hard layers that form after some hours at 20° C. have, after 1 day, a Persoz hardness of 86 s at 20° C. on the glass plate, measured with a TY 5853 pendulum damping tester (BYK-Chemie) according to Persoz. After a 7-day cure at 20° C. the Persoz hardness has increased to 197 s. The layer on the steel plate then resists contact with 10% aqueous acetic acid for at least 3 months without pitting or without peeling from the plate. The curable composition described above also cures satisfactorily at 20° C./100% relative humidity and at 5° C./45% relative humidity with no or only very minor surface haze.

If 4-nonylphenol is replaced with 0.5 benzyl alcohol in the above formulation, the Persoz hardness obtained after 1 day at 20° C. is 83 s, and after a 7-day cure at 20° C. the Persoz hardness is 292 s. The other properties mentioned, in particular the resistance to 10% acetic acid, are very similar.

What is claimed is:

1. A monocarboxamide of formula I

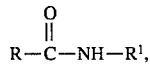

wherein R is a radical of formula

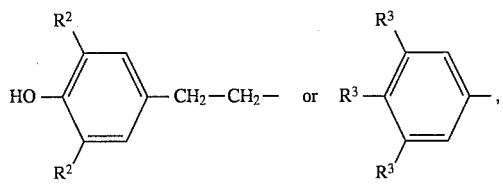

a $C_9$–$C_{19}$alkyl, $C_9$–$C_{19}$alkenyl or a $C_9$–$C_{19}$alkdienyl, wherein each $R^2$ independently of the other is a hydrogen atom or $C_1$–$C_4$alkyl, each $R^3$ independently of one another is a hydrogen atom or a hydroxyl group, and at least one $R^3$ is a hydroxyl group, and $R^1$ is a radical of formula

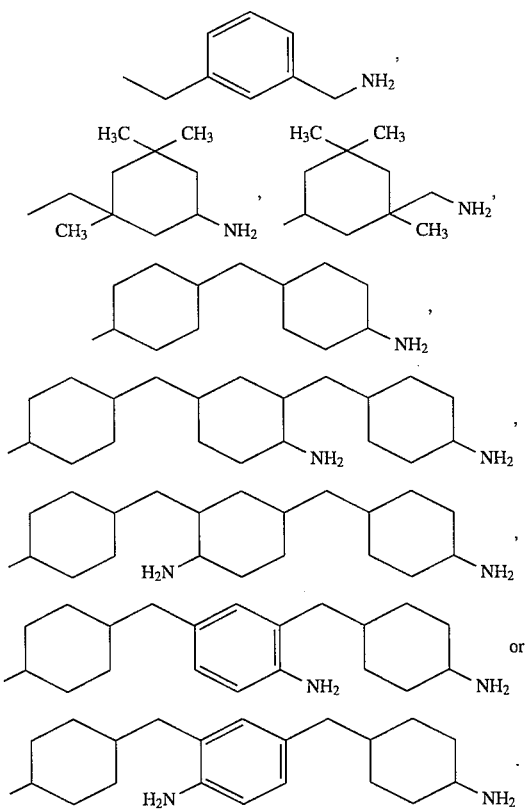

2. A monocarboxamide according to claim 1, wherein R in formula I is a radical of formula

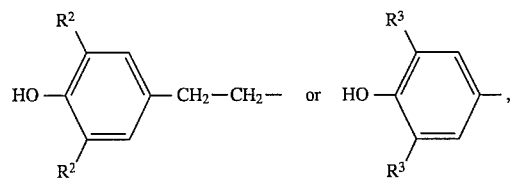

$C_{15}$–$C_{17}$alkyl or $C_{15}$–$C_{17}$alkenyl, wherein each $R^2$ is tert-butyl, and each $R^3$ is a hydrogen atom or each is a hydroxy group.

3. A monocarboxamide according to claim 1, wherein R in formula I is the radical of formula

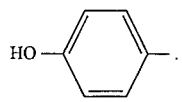
4. A monocarboxamide according to claim 1, wherein $R^1$ in formula I is a radical of formula
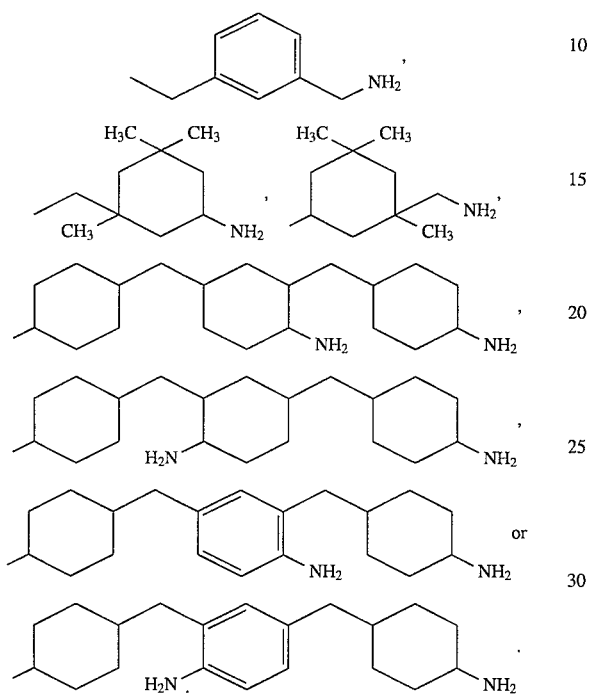
5. A monocarboxamide according claim 1, of formula
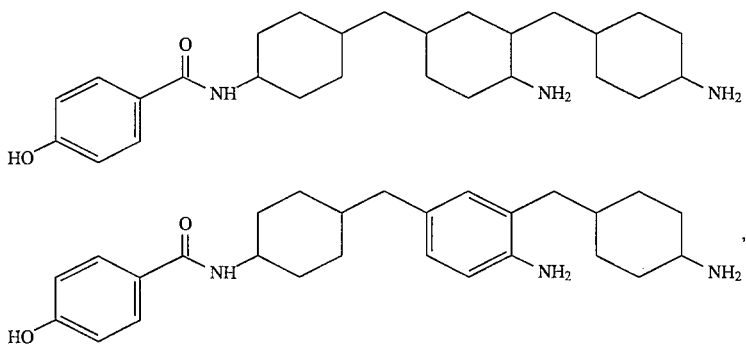
and the structural isomers and stereoisomers thereof.
* * * * *